United States Patent [19]

Jeppesen et al.

[11] Patent Number: 5,227,488

[45] Date of Patent: Jul. 13, 1993

[54] AZA SPIRO DECANE AND USE THEREOF IN TREATING CNS DISORDERS

[75] Inventors: Lone Jeppesen, Virum; Peter H. Andersen, Soborg; Louis B. Hansen; Peter Faarup, both of Vaerlose; John B. Hansen, Lyngby, all of Denmark

[73] Assignee: Novo Nordisk A/S, Bagsvaerd, Denmark

[21] Appl. No.: 590,393

[22] Filed: Sep. 28, 1990

[30] Foreign Application Priority Data

Oct. 9, 1989 [DK] Denmark .............................. 4973/89
Jun. 22, 1990 [DK] Denmark .............................. 1519/90

[51] Int. Cl.$^5$ ..................... A61K 31/40; C07D 401/12
[52] U.S. Cl. ........................................ 546/18; 548/454
[58] Field of Search ....................... 548/454; 546/18; 514/299

[56] References Cited

U.S. PATENT DOCUMENTS 3,860,609 1/1975 Lundt .............................. 260/326.15
4,216,149 8/1980 Asato ........................ 260/326.55 A

FOREIGN PATENT DOCUMENTS 2174703A 11/1986 United Kingdom .

OTHER PUBLICATIONS

Zelesko et al., J. Med. Chem. (1983), 26 pp. 230-237.

Primary Examiner—David B. Springer
Attorney, Agent, or Firm—Steve T. Zelson; Elias J. Lambiris

[57] ABSTRACT

Indole derivatives of formula (I)

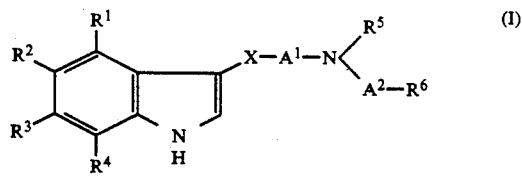

wherein $R^1$, $R^2$, $R^3$ and $R^4$ may be hydrogen or lower alkyl optionally substituted by halogen; X represents oxygen or sulfur; $A^1$ represents a straight or branched alkylene chain containing from 2 to 4 carbon atoms; $R^5$ is hydrogen or a straight or branched alkyl group; $A^2$ is a straight or branched, saturated or unsaturated hydrocarbon chain containing from 2 to 6 carbon atoms; and $R^6$ is selected from a group consisting of various structures, have been found to exhibit central nervous system activities.

7 Claims, No Drawings

AZA SPIRO DECANE AND USE THEREOF IN TREATING CNS DISORDERS

This invention is in the field of pharmaceutical agents exhibiting central nervous system (CNS) activities. More specifically, the invention relates to novel indole derivatives, to a process for their preparation, to pharmaceutical compositions comprising the compounds, and to methods of treating therewith. The novel indole derivatives are potentially suitable for counteracting (including preventing, relieving and curing) certain CNS disorders.

It has long been known that serotonin (5-hydroxytryptamine, hereinafter referred to as 5-HT) is a neurotransmitter in the central nervous system. In particular, over the last decade intensive pharmacological research directed to serotonergic neurotransmitter functions has taken place. It is now generally accepted that in the CNS there are at least five different subtypes of 5-HT binding sites or receptors, which types are identifiable as $5-HT_{1A}$, $5-HT_{1B}$, $5-HT_{1C}$, $5-HT_2$ and $5-HT_3$, respectively. Differentiation of the 5-HT receptor subtypes is mainly based on their binding characteristics as characterized by specific radio ligands. For example, the ligand 8-hydroxy-2-(di-n-propylamino)tetralin (8-OH-DPAT) binds with high affinity to $5-HT_{1A}$ receptors, while another ligand, a 2,4(1H,3H)-quinazolinedione derivative (adopted name: ketanserin) exhibits high affinity for the $5-HT_2$ receptor subtype. It is worth noting that none of these synthetic ligands have any chemical resemblance whatsoever to the physiological binding partner, i.e. 5-HT. For a recent review of 5-HT receptorligand interactions reference is made to J. R. Fozard: Trends in Pharmacol. Sci. 8 (1987), 501–506.

A variety of indole derivatives which are chemically closer related to 5-HT, such as RU 24969, which is a 3-(tetrahydropyridin-4-yl)-indole (Ann. Reports Med. Chem. 21 (1986), 42–43) have high affinity for $5-HT_1$ recognition sites, but generally they show only limited capacity to discriminate between the $5-HT_{1A}$ and $5-HT_{1B}$ receptor subtypes.

It has now surprisingly been observed that compounds of the general formula (I) hereinafter bind with high affinity to 5-HT receptors and, furthermore, that some of the compounds exhibit substantially higher affinity for the $5-HT_{1A}$ subtype than many of the synthetic ligands known heretofore. Based on their binding specificity these compounds may be classified as extremely potent and specific $5-HT_{1A}$ agonists and, as such, of potential utility for the treatment of disorders associated with serotonergic dysfunctions. Such dysfunctions may be involved in the impairment of thermoregulation, memory function, sleep and satiety control of the consumption of feed and/or beverage, which may include alcohol. They may also play a role in the development of hypertension, hyperemesis, ischemia and of such mental states as depression and/or anxiety.

Thus the present invention provides noel indole derivatives of the general formula (I):

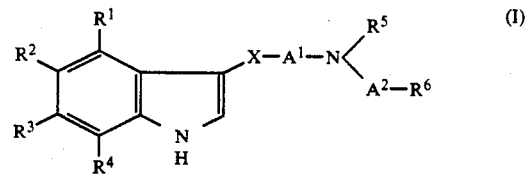

wherein $R^1$, $R^2$, $R^3$ and $R^4$, which may be the same or different, each is selected from the group consisting of hydrogen; lower alkyl containing from 1 to 4 carbon atoms, in which one or more hydrogen atoms may be substituted by halogen, e.g. $CF_3$; $OR^7$ or $—COOR^7$ in which $R^7$ is hydrogen, $C_{1-4}$-alkyl, aryl or aralkyl; halogen, e.g. chlorine; and the group

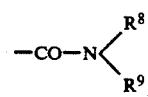

wherein $R^8$ and $R^9$ may be the same or different, each representing hydrogen or lower alkyl containing from 1 to 4 carbon atoms; X represents oxygen or sulfur; $A^1$ represents a straight or branched alkylene chain containing from 1 to 4 carbon atoms; $R^5$ is hydrogen or a straight or branched $C_{1-5}$-alkyl group; $A^2$ is a straight or branched saturated or unsaturated hydrocarbon chain containing from 2 to 6 carbon atoms; and $R^6$ is selected from the group consisting of

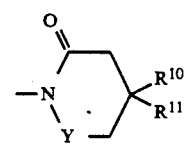

wherein Y is a carbonyl group (C=O) or a sulfonyl group ($SO_2$); $R^{10}$ and $R^{11}$, which may be the same or different, each represents a $C_{1-3}$-alkyl group, or $R^{10}$ and $R^{11}$ together represent a tetra- or pentamethylene chain, thereby forming together with the heterocyclic ring an azaspirodecanedione/trione or -undecanedione/trione ring structure;

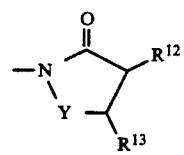

wherein Y is C=O or $SO_2$; $R^{12}$ and $R^{13}$, which may be the same or different, each represents a $C_{1-3}$-alkyl group, or $R^{12}$ and $R^{13}$ together with their neighbouring carbon atoms form a 5- or 6-membered saturated or nonsaturated ring fused to the 5-membered ring;

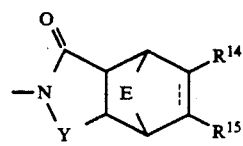

wherein Y is C=O or $SO_2$; E is $—CH_2—$, $—CH_2—CH_2—$, $—CH=CH—$, $—O—$ or $—S—$ and the dotted line represents optional unsaturation; $R^{14}$ and $R^{15}$, which may be the same or different, each represents hydrogen, a $C_{1-3}$-alkyl group, or $R^{14}$ and $R^{15}$ together with their neighbouring carbon atoms form a cyclopropane, cyclobutane, cyclobutene, cyclohexane or cyclohexene ring fused to the bicyclic ring structure.

The compounds of formula I may be converted into any physiological acceptable salts thereof.

In relation to the definition of Y it is known that in the present biological system the $SO_2$-substituent is a bioisoster to the imid-carbonyl-group (see Abou-Gharbia M., J. Med. Chem. 32 (1989), 1024–1033).

The invention includes within its scope all optical isomers of compounds of the general formula (I) and their mixtures including racemic mixtures thereof.

Compounds of the general formula (I) were tested for binding to 5-HT receptors and compared with known ligands by the following procedure:

Rat brain tissue (as specified in the table hereinafter) was homogenized using a Polytron homogenizer. The final pellet was resuspended in 125 vol (tissue wet weight) of buffer.

In all assays incubation was carried out for 10 min at 37° C.

Labelling of the 5-$HT_{1B}$ receptor was complicated by the fact that the available ligand $^3$H-5-HT is nonselective. However, by inclusion of the 5-$HT_{1A}$ selective agent 8-OH-DPAT in the assay, labelling of the 5-$HT_{1A}$ receptor could be avoided and a relatively selective labelling of the 5-$HT_{1B}$ receptor could be accomplished.

Detailed conditions for the receptor binding assay in vitro are tabulated below.

The following results were obtained:

| Compound | Receptor binding $IC_{50}$ (nM) 5-$HT_{1A}$ | 5-$HT_{1B}$ | 5-$HT_2$ | Adenylatcyclase $IC_{50}$ (nM) | Eff (%) |
| --- | --- | --- | --- | --- | --- |
| buspirone | 20 | above 1000 | 1050 | 125 | 70 |
| gepirone | 248 | above 1000 | above 1000 | 1000 | 80 |
| ipsapirone | 25 | above 1000 | above 1000 | 850 | 80 |
| 8-OH-DPAT | 3.4 | 1100 | above 1000 | 80 | 95 |
| Example 3 | 40 | 233 | 613 | 10 | 70 |
| Example 6 | 34 | above 1000 | above 1000 | 20 | 70 |
| Example 8 | 33 | above 1000 | above 1000 | 30 | 90 |
| Example 9 | 20 | 156 | above 1000 | 140 | 100 |
| Example 10 | 8 | above 1000 | above 1000 | 23 | 80 |
| Example 12 | 17 | above 1000 | above 1000 | 240 | 100 |
| Example 23 | 0.6 | above 1000 | above 1000 | 1.8 | 100 |
| Example 24 | 6.9 | above 1000 | above 1000 | 4 | 100 |

The present invention also provides a process for preparing the compounds of the general formula (I) and physiologically acceptable salts thereof, which process is outlined hereinafter.

A compound of the general formula (II)

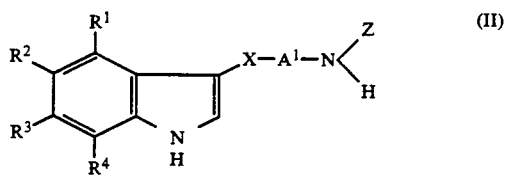

wherein $R^1$, $R^2$, $R^3$, $R^4$, X, and $A^1$ are as defined for formula (I), and Z represents $R^5$ of formula (I) or a group convertible into hydrogen (during such an alkylation process the indole nitrogen and any free hydroxy groups in the benzene ring may be protected, e.g. by benzylation), e.g. benzyl, may be reacted with a compound of the general formula $$L-A^2-R^6 \qquad (III)$$

wherein L represents a leaving group, of which halogen, in particular bromine, is preferred, and $A^2$ and $R^6$ are defined as in connection with formula (I).

Known representatives of compounds of formula (II) are such, in which one of the substituents $R^1$, $R^2$, and $R^3$ represents $OR^7$ while the others are hydrogen and $R^4$ is hydrogen; X and $A^1$ represent oxygen and a dimethylene chain, respectively; Z and $R^7$ being defined

| Receptor type | 5-$HT_{1A}$ | 5-$HT_{1B}$ | 5-$HT_2$ |
| --- | --- | --- | --- |
| Ligand | $^3$H-8OH-DPAT | $^3$H-5-HT | $^3$H-ketanserin |
| Tissue | frontal cortex Hippocampus | frontal cortex Hippocampus striatum | frontal cortex |
| Buffer | 50 mM Tris-Citrate (pH 7.4, 30° C.) 120 mM NaCl, 4 mM $MgCl_2$ | 50 mM Tris-HCl (pH 7.4, 37° C.) 120 mM NaCl, 4 mM $CaCl_2$, 4 mM $MgCl_2$ | 50 mM Tris-Citrate (pH 7.4, 30° C.) 120 mM NaCl, 4 mM $MgCl_2$ |
| Centrifugation | 24,000 × g, twice | 24,000 × g, twice | 24,000 × g, once |
| Preincubation | 10 min, 37° C. | 10 min, 37° C. | — |
| Homogenization | 20 ml | 20 ml | 20 ml |
| mg tissue/assay | 10 | 10 | 10 |
| Ligand conc. | 2 nM | 1 nM | 0.4 nM |
| Addition to assay | — | 50 nM 8-OH-DPAT | — |
| Monspec. binding defined with | 10 μM serotonin | 10 μM serotonin | 1 μM cyproheptadine |
| Level of nonspec. binding | 20–30% | 20–25% | 12–18% | as in U.S. Pat. No. 3,860,609. Other examples are compounds where $R^2$ represents $OR^7$ or chlorine while $R^1$, $R^3$ and $R^4$ are hydrogen; X and $A^1$ represent sulfur and a dimethylene chain respectively; Z is hydrogen and $R^7$ is $CH_3$ (J. Med. Chem. 26, 1985, p. 230). The skilled artisan will appreciate that other compounds falling within the scope of formula (II) may be prepared by methods which are generally analogous to those of said U.S. litterature. General methods for the preparation of compounds of formula $$L\text{-}A^2\text{-}R^6$$

are described in British Patent Publication No. 2,174,703A wherefrom by analogy alternative methods for establishing the

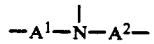

chain can be derived.

The reaction may conveniently be effected in an organic solvent, such as an aprotic solvent, e.g. acetonitrile or dimethylformamide in the presence of a base, for example potassium carbonate. When the leaving group L is different from iodine, being e.g. bromine, the reaction can be conducted in the presence of a salt of hydrogen iodide, e.g. potassium iodide. Usually, the reaction is completed with stirring at a temperature above ambient. The reaction product obtained following, if necessary, after the conversion of Y into hydrogen, may be recovered by conventional means and, if desirable, subjected to purification, e.g. by suitable chromatographic procedures.

The purified reaction product may be converted into a physiologically acceptable salt. Such salts include acid addition salts formed with inorganic or organic acids, for example hydrochlorides, hydrobromides, sulphates, nitrates, oxalates, phosphates, tartrates, citrates, fumarates, maleates, succinates, and sulphonates e.g. mesylates.

If desirable, selected salts may be subjected to further purification by recrystallization.

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compound of the invention is dispensed in unit dosage form comprising 0.05–100 mg in a pharmaceutically-acceptable carrier per unit dosage.

A typical tablet which may be prepared by conventional tabletting techniques contains:

| Active compound | 1.0 mg |
|---|---|
| Lactosum | 67.8 mg Ph.Eur. |
| Avicel | 31.4 mg |
| Amberlite IRP 88 | 1.0 mg |
| Magnesii stearas | 0.25 mg Ph.Eur. |

Due to their high degree of affinity for the 5-HT receptors, the compounds of the invention are extremely useful in the treatment of central nervous system ailments or disorders, when administered in an amount effective for the alleviation, amelioration, or elimination thereof. The important CNS activity of the compounds of the invention as mentioned above, along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the 5-HT receptors, which requires such psychopharmaceutical treatment, if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, and in any event an amount which is effective for the alleviation of such a central nervous system ailment due to their 5-HT receptor affinity. Suitable dosage ranges are 1–200 milligrams daily, 1–100 milligrams daily, and especially 1–30 milligrams daily, depending as usual upon the exact mode of administration, form in which administered, the indication toward which the administration is directed, the subject involved and the body weight of the subject involved, and the preference and experience of the physician or veterinarian in charge.

The following examples serve to illustrate the present invention.

EXAMPLE 1

1-(4-Phthalimidobutyl-1-amino)-2-(3-indolylthio)-ethane, oxalate

A mixture of 3-(2-aminoethylthio)indole, hydrochloride (500 mg; 2.2 mmol) (Zelesko et al., J. Med. Chem. 1983, 26, 230–237), N-(4-bromobutyl)phthalimide (350 mg; 1.5 mmol) and potassium carbonate (700 mg; 5.0 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/methanol (19:1) graduated to ethyl acetate/methanol (4:1). The title compound was isolated as the oxalate. M.p. 122°–126° C. MS (70 eV): m/z 393 (2%, M$^+$), 245 (3), 231 (58), 202 (8), 163 (66), 160 (100), 148 (67), 130 (38), 84 (56), 77 (48), 56 (42).

EXAMPLE 2

1-(4-(3,3-Dimethylglutarimido)butyl-1-amino)-2-(3-indolylthio)-ethane, oxalate A mixture of 3-(2-aminoethylthio)indole, hydrochloride (500 mg; 2.2 mmol), N-(4-bromobutyl)-3,3-dimethylglutarimide (350 mg; 1.27 mmol) and potassium carbonate (700 mg; 5.1 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/methanol (19:1) graduated to ethyl acetate/methanol (4:1). The title compound was isolated as the oxalate. M.p. 112°–115° C. MS (70 eV):m/z 387 (7%, M$^+$), 225 (100), 196 (11), 163 (41), 148 (39), 84 (35), 83 (42), 55 (49).

EXAMPLE 3

1-(4-(7,9-Dioxo-8-azaspiro[4,5]decan-8-yl)butyl-1-amino)2-(3-indolylthio)-ethane, oxalate A mixture of 3-(2-aminoethylthio)indole, hydrochloride (500 mg; 2.2 mmol), 8-(4-bromobutyl)-8-azaspiro[4,5]decane-7,9-dione (375 mg; 1.24 mmol) and potassium carbonate (700 mg; 5.1 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/methanol (19:1) graduated to ethyl acetate/methanol (4:1). The title compound was isolated as the oxalate. M.p. 145,5°–146,0° C. MS (70 eV): m/z 413 (6%, M$^+$), 251 (100), 222 (7), 163 (31), 148 (45), 84 (59), 55 (49).

EXAMPLE 4

1-(4-(1,3-Dioxo-4,6-etheno-1,3,3a,4,4a,5a,6,6a-octahydro-2H-cycloprop[f]isoindol-2-yl)butyl-1-amino)-2-(3-indolylthio)-ethane, oxalate A mixture of 3-(2-aminoethylthio)indole, hydrochloride (500 mg; 2.2 mmol), 2-(4-bromobutyl)-1,3-dioxo-4,6-etheno-1,3,3a,4,4a,5a,6,6a-octahydro-2H-cycloprop[f]isoindole (Abou- Gharbia et al., J. Med. Chem. 1988, 31, 1382–1392) (425 mg; 1.2 mmol) and potassium carbonate (700 mg; 5.1 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/ methanol (19:1) graduated to ethyl acetate/methanol (4:1). The title compound was isolated as the oxalate. M.p. 113°–119° C. MS (70 eV): m/z 435 (7%, M$^+$), 273 (100), 181 (87), 163 (71), 148 (67), 117 (53), 110 (73), 91 (100), 84 (33), 56 (73), 55 (60).

EXAMPLE 5

1-(4-(1,3-Dioxo-4,7-etheno-1,3,3a,4,4a,6a,7,7a-octahydro-2H-cyclobut[f]isoindol-2-yl)butyl-1-amino)-2-(3-indolylthio)-ethane, oxalate A mixture of 3-(2-aminoethylthio)indole, hydrochloride (620 mg; 2.7 mmol), 2-(4-bromobutyl)-1,3-dioxo-4,7-etheno-1,3,3a,4,4a,6a,7,7a-octahydro-2H-cyclobut[f]isoindole (Abou-Gharbia et al., J. Med. Chem. 1988, 31, 1382–1392) (400 mg; 1.2 mmol), potassium carbonate (700 mg; 5.1 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/ methanol (19:1). The title compound was isolated as the oxalate. M.p. 109°–112° C. MS (70 eV): m/z 447 (6%, M$^+$), 285 (100), 256 (10), 214 (8), 163 (51), 148 (55), 110 (46), 84 (39), 56 (75).

EXAMPLE 6

1-(4-(o-Sulfobenzimido)butyl-1-amino)-2-(3-indolylthio)ethane, oxalate

A mixture of 3-(2-aminoethylthio)indole, hydrochloride (500 mg; 2.2 mmol), N-(4-bromobutyl)-o-sulfobenzimide (450 mg; 2.2 mmol) and potassium carbonate (700 mg; 5.1 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate. The title compound was isolated as the oxalate. M.p. 129°–131° C. MS (70 eV): m/z 429 (4%, M+), 267 (63), 246 (37), 238 (4), 196 (21), 183 (100), 148 (73), 84 (100), 76 (100), 55 (80).

EXAMPLE 7

1-(4-(Cis-4-cyclohexen-1,2-dicarboximido)butyl-1-amino)2-(3-indolylthio)-ethane, oxalate A mixture of 3-(2-aminoethylthio)indole, hydrochloride (600 mg; 2.6 mmol), N-(4-bromobutyl)-cis-4-cyclohexen-1,2-dicarboximide (430 mg; 1.2 mmol) and potassium carbonate (850 mg; 6.2 mmol) in acetonitrile (10 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/methanol (25:1). The title compound was isolated as the oxalate. M.p. 115°–116° C. MS (70 eV): m/z 397 (3%, M+), 235 (100), 206 (14), 163 (46), 148 (37), 84 (23), 79 (49), 56 (39).

EXAMPLE 8

1-(4-(7,9-Dioxo-8-azaspiro[4,5]decan-8-yl)butyl-1-amino)-2-(5-methoxy-3-indolylthio)-ethane, oxalate A mixture of 2-(5-methoxy-3-indolylthio)-ethanamine, oxalate (700 mg; 2.2 mmol), 8-(4-bromobutyl)-8-azaspiro[4,5]decane-7,9-dione (425 mg; 1.4 mmol) and potassium carbonate (700 mg; 5.1 mmol) in acetonitrile (15 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined organic phases were dried (MgSO$_4$), filtered and evaporated to give an oil which was flashchromatographed on silicagel 60 eluting with ethyl acetate graduated to ethyl acetate/methanol (20:1). The title compound was isolated as the oxalate. M.p. 120°–123° C. MS (70 eV): m/z 443 (8%, M+), 265 (8), 251 (100), 222 (8), 193 (44), 178 (38), 163 (10), 147 (13), 109 (20), 84 (37), 56 (23).

EXAMPLE 9

1-(4-Phthalimidobutyl-1-amino)-2-(5-methoxy-3-indolylthio)-ethane, oxalate

A mixture of 2-(5-methoxy-3-indolylthio)-ethanamine, oxalate (700 mg; 2.2 mmol), N-(4-bromobutyl)phthalimide (320 mg; 1.1 mmol) and potassium carbonate (750 mg; 5.4 mmol) in acetonitrile (15 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined organic phases were dried (MgSO$_4$), filtered and evaporated to give an oil which was flashchromatographed on silicagel 60 eluting with ethyl acetate. The title compound was isolated as the oxalate. M.p. 134.5°–135.5° C. MS (70 eV): m/z 423 (17%, M+), 245 (14), 231 (100), 202 (14), 193 (73), 178 (45), 160 (92), 147 (21), 130 (18), 84 (35), 56 (20).

EXAMPLE 10

1-(4-(1,3-Dioxo-4,6-etheno-1,3,3a,4,4a,5a,6,6a-octahydro-2H-cycloprop[f]isoindol-2-yl)butyl-1-amino)-2-(3-indolylthio)-ethane, oxalate A mixture of 2-(5-methoxy-3-indolylthio)-ethanamine, oxalate (700 mg; 2.2 mmol), 2-(4-bromobutyl)-1,3-dioxo-4,6-etheno-1,3,3a,4,4a,5a,6,6a-octahydro-2H-cycloprop[f]isoindole (455 mg; 1.4 mmol) and potassium carbonate (700 mg; 5.1 mmol) in acetonitrile (15 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined organic phases were dried (MgSO$_4$), filtered and evaporated to give an oil which was flashchromatographed on silicagel 60 eluting with ethyl acetate graduated to ethyl acetate/methanol (19:1). The title compound was isolated as the oxalate. M.p. 181°–182° C. MS (70 eV): m/z 465 (13%, M+), 315 (7), 287 (10), 273 (100), 244 (2), 193 (51), 181 (61), 178 (45), 147 (17), 110 (48), 91 (68), 84 (18), 56 (25).

EXAMPLE 11

1-(4-(3,6-Epoxy-1,2,3,6-tetrahydrophthalimido)butyl-1-amino)2-(5-methoxy-3-indolylthio)-ethane, oxalate A mixture of 2-(5-methoxy-3-indolylthio)-ethanamine, oxalate (850 mg; 3.8 mmol), N-(4-bromobutyl)-3,6-epoxy-1,2,3,6-tetrahydrophthalimide (1.15 g; 3.8 mmol) and potassium carbonate (530 mg; 3.8 mmol) in acetonitrile (25 ml) was stirred and heated at 80° C. for 16 h. The reaction mixture was evaporated to dryness under reduced pressure. Dichloromethane (25 ml) was added to the residue followed by water (25 ml) and the organic phase was separated. The aqueous phase was extracted with dichloromethane (2×25 ml) and the combined organic phases were dried (Na$_2$SO$_4$), filtered and evaporated to give an oil which was chromatographed on a column of silicagel with ethyl acetate graduated to ethyl acetate/methanol (19:1). The title compound was isolated as the oxalate. M.p. 124°–126° C.

EXAMPLE 12

1-(4-(Cis-4-cyclohexen-1,2-dicarboximido)butyl-1-amino)-2-(5-methoxy-3-indolylthio)-ethane, oxalate A mixture of 2-(5-methoxy-3-indolylthio)-ethanamine, oxalate (890 mg; 4.0 mmol), N-(4-bromobutyl)-cis-4-cyclohexen-1,2-dicarboximide (1.15 g; 4.0 mmol) and potassium carbonate (550 mg; 4 mmol) in acetonitrile (35 ml) was stirred and heated at 80° C. for 16 h. The reaction mixture was evaporated to dryness under reduced pressure. Dichloromethane (35 ml) was added to the residue followed by water (35 ml) and the organic phase was separated. The aqueous phase was extracted with dichloromethane (2×35 ml) and the combined organic phases were dried (Na$_2$SO$_4$), filtered and evaporated to give an oil which was chromatographed on a column of silicagel with ethyl acetate graduated to ethyl acetate/methanol (19:1). The title compound was isolated as the oxalate. M.p. 125°–127° C. MS (70 eV): m/z 427 (8%, M+), 249 (8), 235 (100), 206 (11), 193 (68), 178 (38), 164 (27), 147 (23), 84 (25), 79 (38), 56 (30).

EXAMPLE 13

1-(4-(o-Sulfobenzimido)butyl-1-amino)-2-(5-methoxy-3-indolylthio)-ethane, oxalate A mixture of 2-(5-methoxy-3-indolylthio)-ethanamine, oxalate (850 mg; 3.8 mmol), N-(4-bromobutyl)-o-sulfobenzimide (1.2 g; 3.8 mmol) and potassium carbonate (530 mg; 3.8 mmol) in acetonitrile (25 ml) was stirred and heated at 80° C. for 16 h. The reaction mixture was evaporated to dryness under reduced pressure. Dichloromethane (25 ml) was added to the residue followed by water (25 ml) and the organic phase was separated. The aqueous phase was extracted with dichloromethane (2×25 ml) and the combined organic phases were dried (Na$_2$SO$_4$), filtered and evaporated to give an oil which was chromatographed on a column of silicagel with ethyl acetate graduated to ethyl acetate/methanol (19:1). The title compound was isolated as the oxalate. M.p. 122°–124° C. MS (70 eV): m/z 459 (2%, M+), 281 (2), 267 (14), 238 (2), 193 (7), 183 (11), 178 (8), 147 (4), 84 (100), 55 (7).

EXAMPLE 14

1-(4-(3,3-Dimethylglutarimido)butyl-1-amino)-2-(5-methoxy3-indolylthio)-ethane, oxalate A mixture of 2-(5-methoxy-3-indolylthio)-ethanamine, oxalate (890 mg; 4.0 mmol), N-(4-bromobutyl)-3,3-dimethylglutarimide (1.1 g; 4 mmol) and potassium carbonate (550 mg; 4.0 mmol) in acetonitrile (35 ml) was stirred and heated at 80° C. for 16 h. The reaction mixture was evaporated to dryness under reduced pressure. Dichloromethane (35 ml) was added to the residue followed by water (35 ml) and the organic phase was separated. The aqueous phase was extracted with dichloromethane (2×35 ml) and the combined organic phases were dried (Na$_2$SO$_4$), filtered and evaporated to give an oil which was chromatographed on a column of silicagel with ethyl acetate. The title compound was isolated as the oxalate. M.p. 107°–109° C. MS (70 eV): m/z 417 (7%, M+), 239 (8), 225 (100), 193 (51), 178 (30), 154 (6), 147 (14), 84 (38), 55 (35).

EXAMPLE 15

1-(4-(1,3-Dioxo-4,7-etheno-1,3,3a,4,4a,6a,7,7a-octahydro-2H-cyclobut[f]isoindol-2-yl)butyl-1-amino)-2-(5-methoxy-3-indolylthio)-ethane, oxalate A mixture of 2-(5-methoxy-3-indolylthio)-ethanamine, oxalate (890 mg; 4.0 mmol), 2-(4-bromobutyl)-1,3-dioxo-4,7-etheno-1,3,3a,4,4a,6a,7,7a-octahydro-2H-cyclobut[f]isoindole (1.35 g; 4.0 mmol) and potassium carbonate (550 mg; 4.0 mmol) in acetonitrile (40 ml) was stirred and heated at 80° C. for 16 h. The reaction mixture was evaporated to dryness under reduced pressure. Dichloromethane (40 ml) was added to the residue followed by water (40 ml) and the organic phase was separated. The aqueous phase was extracted with dichloromethane (2×40 ml) and the combined organic phases were dried (MgSO$_4$), filtered and evaporated to give an oil which was chromatographed on a column of silicagel with ethyl acetate. The title compound was isolated as the oxalate. M.p. 118°–119° C. MS (70 eV): m/z 477 (4%, M+), 299 (8), 285 (100), 256 (13), 214 (9), 193 (76), 178 (42), 147 (23), 110 (45), 84 (39), 55 (32).

EXAMPLE 16

1-(4-(7,9-Dioxo-8-azaspiro[4,5]decan-8-yl)butyl-1-amino)-2-(5-chloro-3-indolylthio)-ethane, oxalate A mixture of 2-(5-chloro-3-indolylthio)-ethanamine (Zelesko et al., J. Med. Chem. 1983, 26, 230–237) (150 mg; 0.7 mmol), 8-(4-bromobutyl)-8-azaspiro[4,5]decane-7,9-dione (200 mg; 0.7 mmol) and potassium carbonate (280 mg; 2.0 mmol) in acetonitrile (10 ml) was stirred and heated at 80° C. for 3 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil, which was flashchromatographed on silica gel 60 eluting with ethyl acetate/methanol (19:1). The title compound was isolated as the oxalate. M.p. 150°–153° C.

EXAMPLE 17

1-(4-Phthalimidobutyl-1-amino)-2-(5-chloro-3-indolylthio)ethane, oxalate

A mixture of 2-(5-chloro-3-indolylthio)-ethanamine, oxalate (950 mg; 3 mmol), N(4-bromobutyl)phthalimide (850 mg; 3 mmol) and potassium carbonate (830 mg; 6 mmol) in acetonitrile (50 ml) was stirred and heated at 80° C. for 20 h. The reaction mixture was evaporated to dryness under reduced pressure. Dichloromethane (50 ml) was added to the residue followed by water (50 ml) and the organic phase was separated. The aqueous phase was extracted with dichloromethane (2×50 ml) and the combined dichloromethane phases were dried (MgSO$_4$), filtered and evaporated to give an oil which was flashchromatographed on silica gel 60 eluting with ethyl acetate. The title compound was isolated as the oxalate. M.p. 115°–118° C. MS (70 eV): m/z 428 (20%, M+), 427 (35, M-1), 276 (49), 245 (31), 231 (100), 202 (100), 197 (100), 182 (100), 160 (100), 148 (77), 130 (100), 84 (100), 77 (100), 70 (100), 56 (100).

EXAMPLE 18

1-(4-(1,3-Dioxo-4,6-etheno-1,3,3a,4,4a,5a,6,6a-octahydro-2H-cycloprop[f]isoindol-2-yl)butyl-1-amino)-2-(5-chloro-3-indolylthio)-ethane, oxalate A mixture of 2-(5-chloro-3-indolylthio)-ethanamine, oxalate (900 mg; 4 mmol), 2-(4-bromobutyl)-1,3-dioxo-4,6etheno-1,3,3a,4,4a,5a,6,6a-octahydro-2H-cycloprop[f]isoindole (1.3 g; 4 mmol) and potassium carbonate (1.1 g; 8 mmol) in acetonitrile (50 ml) was stirred and heated at 80° C. for 20 h. The reaction mixture was evaporated to dryness under reduced pressure. Dichloromethane (50 ml) was added to the residue followed by water (50 ml) and the organic phase was separated. The aqueous phase was extracted with dichloromethane (2×50 ml) and the combined dichloromethane phases were dried (MgSO$_4$), filtered and evaporated to give an oil which was flashchromatographed on silica gel 60 eluting with ethyl acetate. The title compound was isolated as the oxalate. M.p. 125°–127° C. MS (70 eV): m/z 470 (9%, M+), 469 (20, M-1), 318 (17), 287 (14), 273 (100), 244 (7), 226 (18), 197 (100), 182 (100), 152 (100), 117 (100), 110 (100), 84 (100), 70 (100), 56 (100).

EXAMPLE 19

1-(4-(1,3-Dioxo-4,7-etheno-1,3,3a,4,4a,6a,7,7a-octahydro-2H-cyclobut[f]isoindol-2-yl)butyl-1-amino)-2-(5-chloro-3-indolylthio)-ethane, oxalate A mixture of 2-(5-chloro-3-indolylthio)-ethanamine, oxalate (950 mg; 3 mmol), 2-(4-bromobutyl)-1,3-dioxo-4,7-etheno-1,3,3a,4,4a,6a,7,7a-octahydro-2H-cyclobut[f]isoindole (1.0 g; 3 mmol) and potassium carbonate (830 mg; 6 mmol) in acetonitrile (50 ml) was stirred and heated at 80° C. for 20 h. The reaction mixture was evaporated to dryness under reduced pressure. Dichloromethane (50 ml) was added to the residue followed by water (50 ml) and the organic phase was separated. The aqueous phase was extracted with dichloromethane (2×50 ml) and the combined dichloromethane phases were dried (MgSO$_4$), filtered and evaporated to give an oil which was flashchromatographed on silica gel 60 eluting with ethyl acetate. The title compound was isolated as the oxalate. M.p. 126°-128° C. MS (70 ev): m/z 482 (1.5%, M+), 481 (4, M-1), 330 (3), 313 (3), 299 (3), 285 (100), 256 (7), 226 (4), 197 (11), 183 (11), 152 (14), 148 (11), 129 (18), 110 (22), 84 (20), 70 (18), 56 (20).

EXAMPLE 20

1-(4-(o-Sulfobenzimido)butyl-1-amino)-2-(5-chloro-3-indolylthio)-ethane, oxalate A mixture of 2-(5-chloro-3-indolylthio)-ethanamine, oxalate (950 mg; 3 mmol), N-(4-bromobutyl)-o-sulfobenzimide (950 mg; 3 mmol) and potassium carbonate (830 mg; 6.0 mmol) in acetonitrile (50 ml) was stirred and heated at 80° C. for 20 h. The reaction mixture was evaporated to dryness under reduced pressure. Dichloromethane (50 ml) was added to the residue followed by water (50 ml) and the organic phase was separated. The aqueous phase was extracted with dichloromethane (2×50 ml) and the combined dichloromethane phases were dried (MgSO$_4$), filtered and evaporated to give an oil which was flashchromatographed on silica gel 60 eluting with ethyl acetate. The title compound was isolated as the oxalate. M.p. 119°-120° C. MS (70 ev): m/z 464 (4%, M+), 46 (14, M-1), 309 (46), 268 (85), 267 (100), 238 (41), 228 (6), 197 (100), 196 (100), 148 (13), 105 (72), 77 (61), 57 (56).

EXAMPLE 21

1-(4-(Cis-4-cyclohexen-1,2-dicarboximido)butyl-1-amino)-2-(5-chloro-3-indolylthio)-ethane, oxalate A mixture of 2-(5-chloro-3-indolylthio)-ethanamine, oxalate (950 mg; 3 mmol), N(4-bromobutyl)-cis-4-cyclohexen-1,2-dicarboximide (860 mg; 3 mmol) and potassium carbonate (830 mg; 6 mmol) in acetonitrile (50 ml) was stirred and heated at 80° C. for 20 h. The reaction mixture was evaporated to dryness under reduced pressure. Dichloromethane (50 ml) was added to the residue followed by water (50 ml) and the organic phase was separated. The aqueous phase was extracted with dichloromethane (2×50 ml) and the combined dichloromethane phases were dried (MgSO$_4$), filtered and evaporated to give an oil which was flashchromatographed on silica gel 60 eluting with ethyl acetate. The title compound was isolated as the oxalate. M.p. 120.5°-123° C. MS (70 ev): m/z 432 (13%, M+), 431 (27, M-1), 280 (24), 236 (100), 235 (100), 206 (98), 197 (100), 182 (100), 164 (100), 152 (100), 110 (31), 70 (97).

EXAMPLE 22

1-(3-(1,3-Dioxo-4,6-etheno-1,3,3a,4,4a,5a,6,6a-octahydro-2H-cycloprop[f]isoindol-2-yl)propyl-1-amino)-2-(3-indolylthio)-ethane, oxalate A mixture of 3-(2-aminoethylthio)indole, hydrochloride (1000 mg; 4.4 mmol), 2-(4-bromobutyl)-1,3-dioxo-4,6-etheno-1,3,3a,4,4a,5a,6,6a-octahydro-2H-cycloprop[f]isoindole (1.35 g; 4.4 mmol) and potassium carbonate (1.2 g ; 8.7 mmol) in acetonitrile (30 ml) was stirred and heated at 80° C. for 16 h. The reaction mixture was evaporated to dryness under reduced pressure. Chloroform (30 ml) was added to the residue followed by water (30 ml) and the organic phase was separated. The aqueous phase was extracted with chloroform (2×30 ml) and the combined chloroform phases were dried (MgSO$_4$), filtered and evaporated to give an oil which was flashchromatographed on silica gel 60 eluting with ethyl acetate. The title compound was isolated as the oxalate. M.p. 191° C. MS (70 eV): m/z 421 (8%, M+), 259 (69), 163 (43), 148 (52), 117 (49), 110 (35), 91 (100), 70 (48), 56 (54).

EXAMPLE 23

1-(4-(7,9-Dioxo-8-azaspiro[4,5]decan-8-yl)butyl-1-amino)-2-(5-methoxy-3-indolyloxy)-ethane, oxalate A mixture of 8-(4-bromobutyl)-8-azaspiro[4,5]decane-7,9-dione (2.0 g; 0.0066 mole), 2-(5-methoxy-3-indolyloxy)ethanamine (3.2 g; 0.013 mole), potassium carbonate (1.82 g; 0.013 mole), anhydrous potassium iodide (100 mg) and acetonitrile (50 ml) was stirred and heated at 80° C. for 16 h. The reaction mixture cooled to 20° C., filtered and the filtrate evaporated to dryness under reduced pressure. The residue was dissolved in dichloromethane/methanol (20:1) and chromatographed on silica gel (Licroprepn ® 60) using dichloromethan/methanol (20:1) as eluent. The appropriate fractions were combined and evaporated to dryness under reduced pressure, and freeze dried to give an amorphe product ; R$_f$=0.15 (Merck silica Gel Plate F$_{254}$, dichloromethane/methanol (10:1), $^1$H-NMR (400 MHz, CDCl$_3$, TMS): 1.48 (m, 4H), 1.56 (m, 4H), 1.68 (m, 4H), 2.58 (s, 4H), 2.76 (t, 2H), 3.04 (t, 2H), 3.78 (t, 2H+H), 3.88 (s, 3H), 4.10 (t, 2H), 6.70 (d, 1H), 6.84 (dd, 1H), 7.08 (d, 1H), 7.16 (d, 1H), 7.56 (s, 1H).

EXAMPLE 24

1-(4-(1,3-Dioxo-4,7-etheno-1,3,3a,4,4a,6a,7,7a-octahydro-2H-cyclobut[f]isoindol-2-yl)butyl-1-amino)-2-(5-methoxy-3-indolyloxy)-ethane, oxalate A mixture of 2-(5-methoxy-3-indolyloxy)-ethanamine (515 mg; 2.5 mmol), 2-(4-bromobutyl)-1,3-dioxo-4,7-etheno-1,3,3a,4,4a,6a,7,7a-octahydro-2H-cyclobut[f]isoindole (500 mg; 1.5 mmol) and potassium carbonate (700 mg; 5 mmol) in acetonitrile (15 ml) was stirred and heated at 80° C. for 16 h. The reaction mixture was evaporated to dryness under reduced pressure. Chloroform (15 ml) was added to the residue followed by water (15 ml) and the organic phase was separated. The aqueous phase was extracted with chloroform (2×15 ml) and the combined chloroform phases were dried (MgSO$_4$), filtered and evaporated to give an oil which was flashchromatographed on silica gel 60 eluting with ethyl acetate/methanol (30:1). The title compound was isolated as the oxalate. M.p. 106°-110° C. MS (70 ev):

m/z 461 (83%, M+), 430 (89), 299 (6), 285 (14), 256 (21), 247 (7), 219 (100), 189 (69), 147 (65), 129 (61), 110 (72).

EXAMPLE 25

1-(4-(1,3-Dioxo-4,6-etheno-1,3,3a,4,4a,5a,6,6a-octahydro-2H-cycloprop[f]isoindol-2-yl)butyl-1-amino)-2-(5-methoxy-3-indolyloxy)-ethane, oxalate A mixture of 2-(5-methoxy-3-indolyloxy)-ethanamine (1.2 g; 4 mmol), 2-(4-bromobutyl)-1,3-dioxo-4,6-etheno-1,3,3a,4,4a,5a,6,6a-octahydro-2H-cycloprop[f]isoindole (1.3 g; 4 mmol) and potassium carbonate (1.2 g; 9 mmol) in acetonitrile (40 ml) was stirred and heated at 80° C. for 16 h. The reaction mixture was evaporated to dryness under reduced pressure. The residue was added dichloromethane, filtered and evaporated to give an oil, which was flashchromatographed on silica gel 60 eluting with ethyl acetate. The title compound was isolated as the oxalate. M.p. 104°–105° C. MS (70 eV): m/z 449 (100%, M+), 418 (45), 326 (28), 273 (11), 219 (18), 91 (38).

EXAMPLE 26

1-(4-(o-Sulfobenzimido)butyl-1-amino)-2-(5-methoxy-3-indolyloxo)-ethane, oxalate A mixture of 2-(5-methoxy-3-indolyloxy)-ethanamine (1.8 g; 6 mmol), N-(4-bromobutyl)-o-sulfobenzimide 955 mg; 3 mmol), potassium carbonate (1.2 g; 9 mmol) and anhydrous potassium iodide (80 mg) in acetonitrile (40 ml) was stirred and heated at 80° C. for 16 h. The reaction mixture was evaporated to dryness under reduced pressure. The residue was added dichloromethane, filtered and evaporated to give an oil, which was flashchromatographed on silica gel 60 eluting with ethyl acetate. The title compound was isolated as the oxalate. M.p. 149°–150° C. MS (70 eV): m/z 443 (56%, M+), 412 (100), 219 (23), 196 (25), 189 (10), 175 (10), 147 (13), 104 (10.

EXAMPLE 27

1-(4-Phthalimidobutyl-1-amino)-2-(5-methoxy-3-indolyloxy)ethane, oxalate

A mixture of 2-(5-methoxy-3-indolyloxy)-ethanamine (1.8 g; 6 mmol), N-(4-bromobutyl)phthalimide (850 mg; 3 mmol), potassium carbonate (1.2 g; 9 mmol) and anhydrous potassium iodide (80 mg) in acetonitrile (40 ml) was stirred and heated at 80° C. for 16 h. The reaction mixture was evaporated to dryness under reduced pressure. The residue was added dichloromethane, filtered and evaporated to give an oil, which was flash-chromatographed on silica gel 60 eluting with ethyl acetate. The title compound was isolated as the oxalate. M.p. 163°–164° C. MS (70 eV): m/z 407 (93%, M+), 376 (100), 245 (4), 231 (11), 219 (36), 202 (14), 189 (23), 175 (18), 160 (86), 147 (23), 130 (20).

EXAMPLE 28

1-(4-(Cis-4-cyclohexen-1,2-dicarboximido)butyl-1-amino)-2-(5-methoxy-3-indolyloxy)-ethane, oxalate A mixture of 2-(5-methoxy-3-indolyloxy)-ethanamine (1.8 g; 6 mmol), N-(4-bromobutyl)-cis-4-cyclohexen-1,2-dicarboximide (860 mg; 3 mmol), potassium carbonate (1.2 g; 9 mmol) and anhydrous potassium iodide (80 mg) in acetonitrile (40 ml) was stirred and heated at 80° C. for 16 h. The reaction mixture was evaporated to dryness under reduced pressure. The residue was added dichloromethane, filtered and evaporated to give an oil, which was flash-chromatographed on silica gel 60 eluting with ethyl acetate. The title compound was isolated as the oxalate. M.p. 125°–127° C. MS (70 eV): m/z 411 (69%, M+), 380 (100), 235 (14), 219 (46), 206 (24), 189 (27), 175 (27), 164 (20), 147 (34), 79 (70).

EXAMPLE 29

1-(4-(3,3-Dimethylglutarimido)butyl-1-amino)-2-(5-methoxy-3-indolyloxy)-ethane, oxalate A mixture of 2-(5-methoxy-3-indolyloxy)-ethanamine (1.2 g; 4 mmol), N-(4-bromobutyl)-3,3-dimethylglutarimide (550 mg; 2 mmol), potassium carbonate (830 mg; 6 mmol) and anhydrous potassium iodide (60 mg) in acetonitrile (25 ml) was stirred and heated at 80° C. for 16 h. The reaction mixture was evaporated to dryness under reduced pressure. The residue was added dichloromethane, filtered and evaporated to give an oil, which was flashchromatographed on silica gel 60 eluting with ethyl acetate. The title compound was isolated as the oxalate. M.p. 106°–108° C. MS (70 eV): m/z 401 (66%, M+), 370 (100), 239 (4), 225 (10), 219 (55), 196 (13), 189 (34), 175 (26), 159 (17), 147 (32), 83 (66).

EXAMPLE 30

1-(5-(1,3-Dioxo-4,6-etheno-1,3,3a,4,4a,5a,6,6a-octahydro-2H-cycloprop[f]isoindol-2-yl)pentyl-1-amino)-2-(3-indolylthio)-ethane, oxalate A mixture of 3-(2-aminoethylthio)indole, hydrochloride (1.0 g; 4.4 mmol), 2-(5-bromopentyl)-1,3-dioxo-4,6-etheno-1,3,3a,4,4a,5a,-6,6a-octahydro-2H--cycloprop[f]isoindole (1.5 g, 4.4 mmol), potassium carbonate (1.2 g; 8.8 mmol) and anhydrous potassium iodide (50 mg) in acetonitrile (50 ml) was stirred and heated at 80° C. for 16 h. The reaction mixture was evaporated to dryness under reduced pressure. Ethyl acetate (50 ml) was added to the residue followed by water (50 ml) and the organic phase was separated. The aqueous phase was extracted with ethyl acetate (2×50 ml) and the combined organic phases were dried (MgSO4), filtered and evaporated to give an oil, which was flash-chromatographed on silica gel 60 eluting with ethyl acetate. The title compound was isolated as the oxalate. M.p. 94°–97° C. MS (70 eV): m/z 449 (18%, M+), 287 (89), 195 (30), 163 (30), 148 (41), 117 (39), 91 (100).

We claim:

1. A compound of formula I

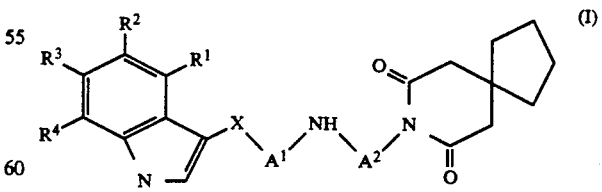

wherein
R$^1$, R$^2$, R$^3$ and R$^4$, which may be the same or different, are hydrogen; C$_{1-4}$-alkyl wherein one or more hydrogen atoms may be substituted by halogen; OR$^7$ or COOR$^7$ wherein R$^7$ is hydrogen or C$_{1-4}$-alkyl; halogen; or the group

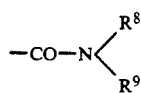

wherein $R^8$ and $R^9$, which may be the same or different, are hydrogen or $C_{1-4}$-alkyl;

X is oxygen or sulfur;

$A^1$ is straight or branched $C_{2-4}$-alkylene chain; and $A^2$ is straight or branched saturated or unsaturated $C_{2-6}$-hydrocarbon chain; or a pharmaceutically acceptable salt thereof.

2. The compound according to claim 1, wherein $A^2$ is butyl, $A^1$ is ethyl, $R^1$, $R^2$ and $R^3$ are hydrogen and/or $R^2$ is hydrogen, methoxy or chlorine.

3. The compound according to claim 1 which is
1-(4-(7,9-dioxo-8-azaspiro[4,5]decan-8-yl)butyl-1-amino)-2-(3-indolylthio)-ethane;
1-(4-(7,9-dioxo-8-azaspiro[4,5]decan-8-yl)butyl-1-amino)-2-(5-methoxy-3-indolylthio)-ethane;
1-(4-(7,9-dioxo-8-azaspiro[4,5]decan-8-yl)butyl-1-amino)-2-(5-methoxy-3-indolyloxy)-ethane; or a pharmaceutically acceptable salt thereof.

4. A pharmaceutical composition for use in treating a central nervous system disorder associated with serotonergic dysfunctions which comprises an effective amount of a compound according to claim 1 together with a pharmaceutically acceptable carrier or diluent.

5. The pharmaceutical composition according to claim 4, which contains between 0.1 mg and 250 mg of the active ingredient per dose unit.

6. A method of treating a central nervous system disorder associated with serotonergic dysfunctions comprising administering to a subject in need thereof an effective amount of a compound according to claim 1.

7. A method of treating a central nervous system disorder associated with serotonergic dysfunctions comprising administering to a subject in need thereof a pharmaceutical composition according to claim 4.

* * * * *